United States Patent
Quinn (10) Patent No.: US 8,216,415 B2
(45) Date of Patent: Jul. 10, 2012

(54) MANUFACTURE OF KINESIOLOGY TAPE

(76) Inventor: Reed M. Quinn, Highland, UT (US)

( * ) Notice: Subject to any disclaimer, the term of this patent is extended or adjusted under 35 U.S.C. 154(b) by 279 days.

(21) Appl. No.: 12/554,203

(22) Filed: Sep. 4, 2009

(65) Prior Publication Data

US 2011/0056621 A1 Mar. 10, 2011

(51) Int. Cl.
*B29C 65/00* (2006.01)
*B32B 37/00* (2006.01)
*B32B 38/04* (2006.01)
*B05D 3/00* (2006.01)
*B05C 1/00* (2006.01)
*B05C 11/00* (2006.01)
*B05C 13/00* (2006.01)

(52) U.S. Cl. ........ 156/270; 156/256; 427/194; 427/197; 118/202; 118/211; 118/50; 118/59; 83/346; 101/127; 101/129

(58) Field of Classification Search .................. 427/194, 427/197; 118/202, 211, 50, 59; 83/346; 156/256, 270; 101/127, 129
See application file for complete search history.

(56) References Cited

U.S. PATENT DOCUMENTS

| | | | | |
|---|---|---|---|---|
| 4,882,004 A | * | 11/1989 | Watson | 156/381 |
| 5,050,497 A | * | 9/1991 | Klemm | 101/124 |
| 5,083,488 A | * | 1/1992 | Stanley et al. | 83/344 |
| 5,782,496 A | | 7/1998 | Casper et al. | |
| 5,842,413 A | * | 12/1998 | Karlyn et al. | 101/128.4 |
| 6,422,848 B1 | | 7/2002 | Allen et al. | |
| 2010/0098846 A1 | * | 4/2010 | Ding et al. | 427/207.1 |

\* cited by examiner

*Primary Examiner* — Linda L Gray
(74) *Attorney, Agent, or Firm* — DLC Patents, PLLC; Dustin L. Call (57) ABSTRACT

An embodiment of the invention includes a continuous feed variable depth die cut for use in cutting kinesiology tape. The die cut includes a housing, including a first opening configured to allow the kinesiology tape to enter the housing and a second opening configured to allow the kinesiology tape to exit the housing. The die cut also includes a roller inside the housing, wherein the roller is configured to rotate as the kinesiology tape passes over the roller and a die formed on the outer surface of the roller, wherein the die includes a cutting edge for cutting the kinesiology tape and wherein the cutting edge is formed in the shape of the strip of kinesiology tape to be cut. The die cut further includes a surface inside the housing, wherein the kinesiology tape passes over the surface when the kinesiology tape is being cut.

6 Claims, 6 Drawing Sheets

MANUFACTURE OF KINESIOLOGY TAPE

CROSS-REFERENCE TO RELATED APPLICATIONS

Not applicable.

BACKGROUND OF THE INVENTION

Kinesiology tape consists of a strip of elastic and non-elastic fibers, usually covered in cotton, which is placed on human skin. Kinesiology tape is useful in therapy to reduce soreness in overused and injured muscles and in rehabilitation to accelerate recovery. The tape can have a lifting effect on the skin which can reduce swelling and inflammation by improving circulation and reduce pain by taking pressure off pain receptors.

Nevertheless, there are a number of drawbacks in the current art regarding the manufacture and production of kinesiology tape. In particular, kinesiology tape is generally sold in large rolls which the consumer must cut before using. However, the tape is often difficult to cut because of its elastic nature. The tape must be cut with a very sharp object, such as sharp scissors, which makes it more difficult for consumers to use in places, such as a gym, where the consumer must carry the means to cut the tape with them.

Additionally, many forms of treatment using kinesiology tape require cutting the tape to wrap the tape, or portions thereof, around a particular joint. Therefore, a consumer must cut a portion of an individual strip in the correct manner for proper application. This is difficult and inconvenient for many consumers who may forgo use of the tape and, therefore, miss its therapeutic and injury preventative uses.

The tape could be cut into individual strips, and or cuts made to the individual strips for proper application, during manufacture using traditional die cutting methods. Nevertheless, this suffers from a number of drawbacks. First, the tape must be stopped while the cutting occurs. Second, cutting individual strips while avoiding cutting the backing is difficult because the thickness of the tape may vary due to the elastic nature of the individual threads. Third, perforations are difficult to achieve without making individual cuts to the interior of the tape.

Additional problems arise in the application of adhesive to the kinesiology tape. A solid coating of adhesive prevents the material from breathing, which retains moisture on the skin, ultimately forcing the tape to fall off the skin. Applying the adhesive in straight tracks makes the tape susceptible to forces pushing across the tracks.

Further, it is difficult to print on the kinesiology tape itself. The tape is a porous material. Therefore, if too much ink is applied to the tape, the printing will smudge and will bleed through the tape. If too little ink is used, the printing will not be visible or the coloring will be wrong.

Accordingly, there are a number of disadvantages in the conventional manufacture of kinesiology tape that can be addressed.

BRIEF SUMMARY OF SOME EXAMPLE EMBODIMENTS

This Summary is provided to introduce a selection of concepts in a simplified form that are further described below in the Detailed Description. This Summary is not intended to identify key features or essential characteristics of the claimed subject matter, nor is it intended to be used as an aid in determining the scope of the claimed subject matter.

An embodiment of the invention includes a continuous feed variable depth die cut for use in cutting kinesiology tape. The die cut includes a housing, including a first opening configured to allow the kinesiology tape to enter the housing and a second opening configured to allow the kinesiology tape to exit the housing. The die cut also includes a roller inside the housing, wherein the roller is configured to rotate as the kinesiology tape passes over the roller and a die formed on the outer surface of the roller, wherein the die includes a cutting edge for cutting the kinesiology tape and wherein the cutting edge is formed in the shape of the strip of kinesiology tape to be cut. The die cut further includes a surface inside the housing, wherein the kinesiology tape passes over the surface when the kinesiology tape is cut.

Another embodiment of the invention includes an adhesive applying device for applying adhesive to backing that will be placed on kinesiology tape. The adhesive applying device includes an applicator, wherein the applicator is configured to apply glue to one surface of the backing. The adhesive applying device also includes a comb, wherein the comb is configured to produce a pattern in the adhesive as the backing moves past the comb, wherein the comb includes a spine and multiple teeth protruding from the spine, wherein the teeth remove adhesive from the backing. The adhesive applying device further includes a shaft attached to the spine and an erratic cam, wherein the erratic cam is configured to move the shaft on the comb to produce motion in the comb and a motor for rotating the erratic cam.

A further embodiment of the invention includes a printing device for printing on kinesiology tape. The printing device includes a surface, wherein the kinesiology tape moves across the surface as the printing occurs, and a tray for holding the ink. The printing device further includes a woven mesh, wherein the woven mesh forms at least a portion of the bottom of the tray. The woven mesh includes an ink-blocking stencil, wherein the stencil includes blocked mesh that prevent the extrusion of ink and an open area of mesh, wherein the open area of the mesh allows the extrusion of ink onto the kinesiology tape. The printing device also includes a squeegee, wherein the squeegee moves across the mesh forcing ink through the open area of the mesh and forces the mesh onto the kinesiology tape.

These and other objects and features of the present invention will become more fully apparent from the following description and appended claims, or may be learned by the practice of the invention as set forth hereinafter.

BRIEF DESCRIPTION OF THE DRAWINGS

To further clarify various aspects of some example embodiments of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which.

DETAILED DESCRIPTION OF SOME EXAMPLE EMBODIMENTS

Reference will now be made to the figures wherein like structures will be provided with like reference designations. It is understood that the figures are diagrammatic and schematic representations of some embodiments of the invention, and are not limiting of the present invention, nor are they necessarily drawn to scale.

Figure 1A:
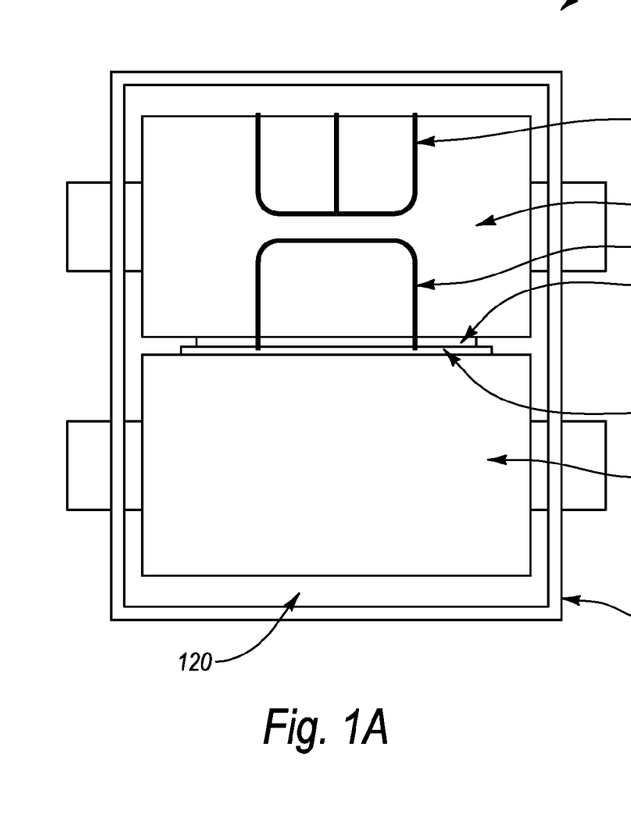
FIG. 1A illustrates a facing view of an example of a continuous form variable depth die cut in accordance with an implementation of the present invention.
Figure 1B:
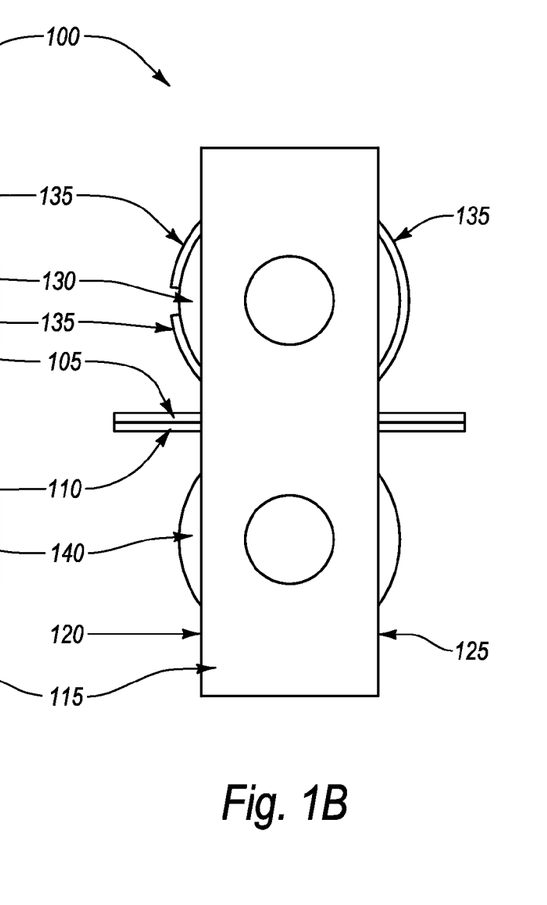
FIG. 1B illustrates a side view of the continuous form variable depth die of FIG. 1A.

FIGS. 1A and 1B illustrate an example of a continuous form variable depth die 100 in accordance with an implementation of the present invention. FIG. 1A illustrates a facing view of the continuous form variable depth die 100. In contrast, FIG. 1B illustrates a side view of the continuous form variable depth die 100. FIGS. 1A and 1B show that, in at least one implementation, the die 100 can cut, shape and form a strip of kinesiology tape 105, and the backing 110 attached to the kinesiology tape 105, during the manufacture thereof. In particular, the die 100 can cut a single large ribbon of kinesiology tape 105 into a number of smaller strips. Additionally or alternatively, the die can cut or perforate the backing 110 of the kinesiology tape 105, allowing a user to separate individual strips of kinesiology tape 105 from one another as needed.

FIGS. 1A and 1B also show that, in at least one implementation, the die 100 includes a housing 115. In particular, the housing 115 can hold the components of the die 100. For example, the housing 115 can ensure that other components of the die 100 remain a standard distance from one another. Keeping the components of the die 100 a standard distance from one another can guarantee that the components do not come in contact with one another unless specifically desired. Additionally, keeping the components of the die 100 a standard distance from one another can also guarantee that any cuts made to the kinesiology tape 105 are a standard depth, as discussed below.

FIGS. 1A and 1B further show that, in at least one implementation, the housing 115 can include a first opening 120 in one of the sides. FIGS. 1A and 1B show that the first opening 120 can include a housing 115 without a cover 115. Additionally or alternatively, the first opening 120 can include a cover in the housing 115, wherein the cover includes one or more openings. In a least one implementation, the first opening 120 can allow one or more large ribbons of kinesiology tape 105 to pass into the housing 115, where the die 100 can cut the kinesiology tape 105 into individual strips.

FIGS. 1A and 1B also show that, in at least one implementation, the die 100 also includes a second opening 125. FIGS. 1A and 1B show that the second opening 125 can allow the individual strips of kinesiology tape 105 to pass out of the die 100. Additionally, FIGS. 1A and 1B show that, the second opening 125 can be in a different side of the housing 115 than the first opening 120. For example, the second opening 125 can be opposite the first opening 120, such that the kinesiology tape 105 can pass straight through the housing 115 and exit after cutting. Additionally or alternatively, the second opening 125 can be in the same side of the housing 115 as the first opening 120.

FIGS. 1A and 1B also show that the die 100 can include a roller 130. In particular, the housing 115 can secure the roller 130 such that the roller 130 can rotate with respect to the housing. In particular, the roller 130 can be wide enough to ensure the proper width of the kinesiology tape 105 after cutting. For example, if the desired width of the kinesiology tape 105 is 50 millimeters, the width of the roller 130 can be 60 millimeters. Likewise, the circumference of the roller 130 can determine the length of the strips of the kinesiology tape 105 after cutting. For example, if the desired length of the strips of kinesiology tape 105 is 255 millimeters with 5 millimeters between strips, the circumference of the roller 130 can be 260 millimeters.

FIGS. 1A and 1B further show that one or more cutting edges 135 can be formed on the roller 130. The one or more cutting edges 135 together form one or more die on the outer circumference of the roller 130 for producing an individual strip of kinesiology tape of the proper size and shape. For example, the cutting edge 135 can include rounded corners, for producing rounded corners on the individual strips of kinesiology tape 105. Additionally or alternatively, different portions of the cutting edge 135 can be different depths. That is, one part of the cutting edge 135 may protrude from the roller 130 to a greater or lesser degree than another portion of the cutting edge 135. Variable depths on the cutting edge 135 can allow different types of cuts to the kinesiology tape 105. Accordingly, strips of kinesiology tape 105 can be cut with different shapes and depths. I.e., some cuts to the kinesiology tape 105 can include straight cuts and some cuts can include rounded cuts. Further, some cuts to the kinesiology tape 105 can go all the all the way through the kinesiology tape 105, whereas some cuts can go partway through the kinesiology tape 105. Moreover, some cuts to the kinesiology tape 105 can be continuous and some cuts to the kinesiology tape 105 can be perforated. Accordingly, the cutting edge 135 can cut the kinesiology tape 105 in any manner desired by the operator and according to the configuration of the cutting edge.

The cutting edge 135 can comprise any material of sufficient strength to remain sharp during the cutting of the kinesiology tape 105. For example, the cutting edge 135 can be made of steel, copper, aluminum or any other material sufficiently strong to retain a cutting surface during use. Additionally or alternatively, the cutting edge 135 can comprise a material that is able to be resharpened when the cutting surface is dulled.

Further, the roller 130 can rotate at the same speed as the kinesiology tape 105 and backing 110 pass through the die 100. In particular, matching the rotation speed of the roller 130 with the speed of the kinesiology tape 105 can allow the kinesiology tape 105 to be cut into strips without stopping the movement of the kinesiology tape 105 as it passes through the die 100. For example, if the kinesiology tape 105 passes through the die 100 at 150 meters/min, the roller 130 can rotate such that the outer edge of the roller is moving at 150 meters/min. Continuing the example above, if the roller 130 is 252 millimeters, the rotation of the roller 130 can be set at 150 meters/min×1/0.252 rotations/meter or ~595 rotations/min. Accordingly, the kinesiology tape 105 can pass through the die 100, without slowing, while the kinesiology tape 105 is cut into individual strips, thus allowing for faster and more efficient cutting of the kinesiology tape 105.

FIGS. 1A and 1B show that, in at least one implementation, the die 100 further includes a surface 140 on which the kinesiology tape 105 can travel. In at least one implementation, the surface 140 is a second roller. In particular, the surface 140 can contain guides which steer the ribbon of kinesiology tape 105 to ensure that the ribbon is cut as desired. I.e., the surface 140 can contain guides such that the lateral placement of the ribbon of kinesiology tape 105 with respect to the cutting edge 135 is fixed. Additionally or alternatively, the kinesiology tape can be pulled along the surface in a manner which keeps the kinesiology tape 105 in the desired position in relation to the roller 130 and the cutting edge 135. Accordingly, the kinesiology tape 105 can be cut into individual strips with high precision.

Additionally or alternatively, the surface 140 can guarantee that the ribbon of kinesiology tape 105 is a predetermined distance from the roller 130, thus providing a precise means for setting the depth that the cutting edge 135 will cut into the kinesiology tape 105. For example, the roller 130 and the surface 140 can be set a distance of 0.08 millimeters from one another. The setting of a precise distance between the roller 130 and the surface 140 can allow for a high degree of precision in the cutting of the kinesiology tape 105. Accordingly, cuts can be made precise enough that the cuts score the backing 110 of the kinesiology tape 105, even though the kinesiology tape 105 is highly flexible and elastic and is difficult to cut using conventional methods.

In at least one implementation, the roller 130 rotates as a ribbon of kinesiology tape 105 enters the housing 110 and passes along the surface 140. If the rotation of roller 130 matches the speed of the ribbon of kinesiology tape 105, the kinesiology tape 105 can be cut to the pattern of the cutting edge 135. That is, the roller 130 rotates, bringing different sections of the cutting edge 135 into contact with the ribbon of kinesiology tape 105 as the kinesiology tape 105 proceeds through the die 100. Accordingly, the kinesiology tape 105 is cut with the desired pattern and exits the die 100.

Accordingly, this method of cutting allows for very precise cutting of the kinesiology tape 105. For example, the kinesiology tape 105 can be cut without cutting the backing 110 of the kinesiology tape 105 if the distance between the roller 130, the cutting edge 135 and the surface 140 is precisely controlled. Accordingly, the ribbon of kinesiology tape 105 can be cut into individual strips with a high degree of precision, while the ribbon of kinesiology tape 105 is moving, thus speeding production. For example, the difference in depths of the cuts made to the kinesiology tape 105 can be 0.01 millimeters, even when cutting elastic material such as kinesiology tape 105.

Figure 2:
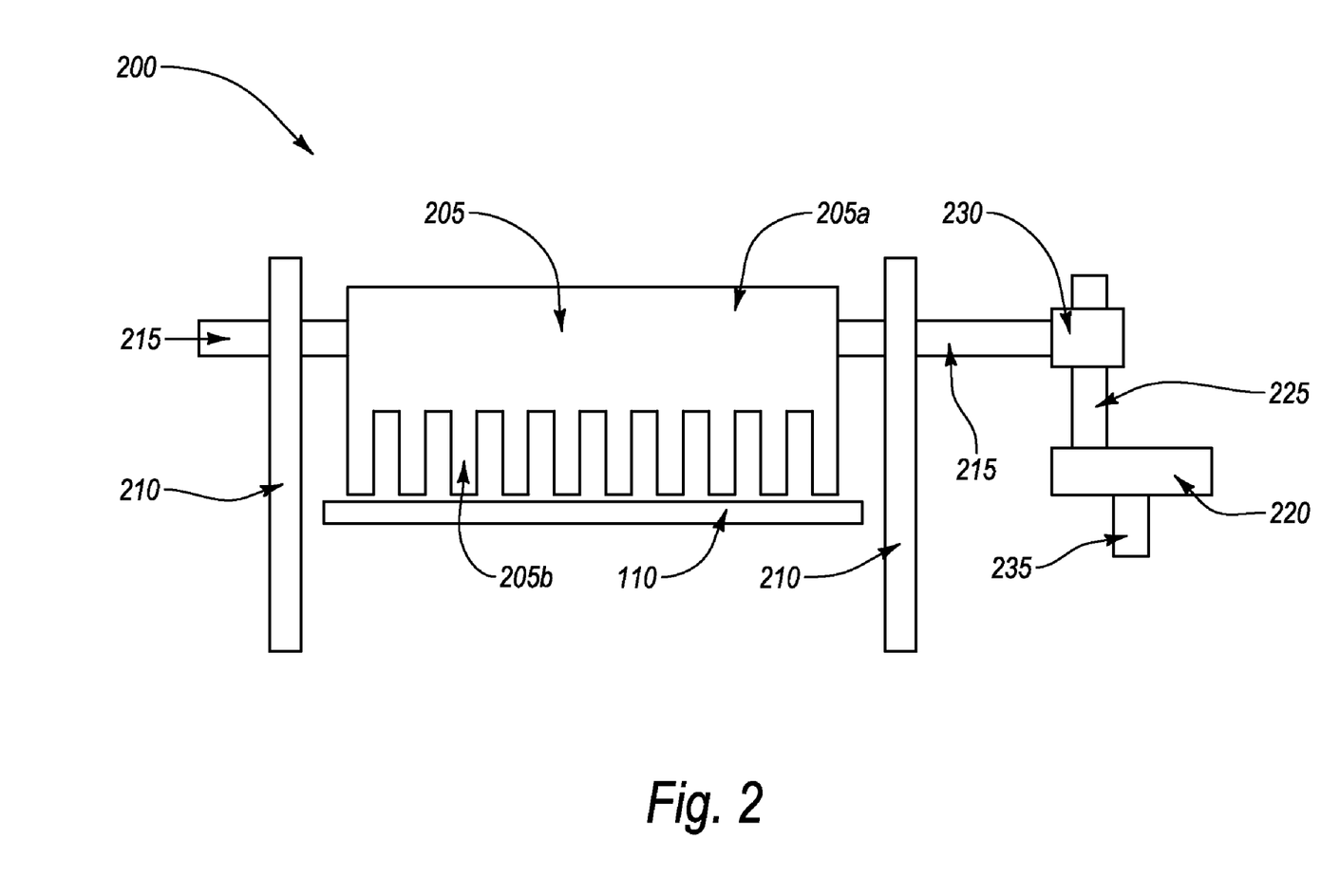
FIG. 2 illustrates an example of an adhesive applicator in accordance with an implementation of the invention.

FIG. 2 illustrates an example of an adhesive applicator 200 in accordance with an implementation of the invention. In at least one implementation, the adhesive applicator 200 can be used to apply adhesive to backing 110 to be applied to a strip of kinesiology tape. Additionally or alternatively, the adhesive applicator 200 can apply adhesive to a strip of kinesiology tape with the backing 110 applied later. Adhesive on a strip of kinesiology tape can allow a user to easily apply the tape as need requires, without additional materials. The backing 110 can protect the adhesive and prevent drying of the solvent until a user is ready to apply the kinesiology tape.

Adhesive can be initially applied to the backing 110 (or the kinesiology tape if so desired) using any preferred method which provides an even coating of adhesive. For example, the adhesive can be sprayed on to the backing 110. Additionally or alternatively, the adhesive can be applied to the backing 110 using a brush. Accordingly, any method of application is acceptable, provided the method applies an even coating of adhesive.

The adhesive can include any adhesive which will allow the kinesiology tape to adhere to the skin of a user without irritating the user's skin. For example, the adhesive can include pressure-sensitive adhesive. Pressure sensitive adhesive is adhesive which forms a bond when pressure is applied. I.e., no solvent, water, activator chemicals, heat or other activating agent is needed to activate the adhesive. In at least one implementation, the degree of bonding is influenced by the amount of pressure which is used to apply the adhesive to the surface of the backing 110.

In at least one implementation, the adhesive can include an adhesive with a main ingredient which is configured to provide the bonding between the kinesiology tape and the user's skin. The main ingredient can include a single compound or a mixture of compounds. For example, the main ingredient can include polyacrylate. Additionally or alternatively, the adhesive can include a solvent which is configured to evaporate or break down after application of the adhesive, leaving the main ingredient behind. For example the adhesive can include about 50% of the main ingredient with the rest of the adhesive comprising solvent. In at least one implementation, the solvent can include ethyl acetate FIG. 2 shows that the adhesive applicator 200 can include a comb 205. The comb removes a portion of the previously applied adhesive from the backing 110. Removing a portion of the previously applied adhesive from the backing 110 during manufacture can ensure that the kinesiology tape adheres better to a user's skin during application of the kinesiology tape. For example, removing a portion of the adhesive from the backing 110 during manufacture can allow the kinesiology tape to breathe. I.e., allow the moisture from the user's skin to pass through the kinesiology tape. Breathing is not possible with a water resistant adhesive covering the entire surface of the kinesiology tape.

In at least one implementation, the comb 205 can be made of any material sufficiently rigid that the teeth 205b can remove the adhesive from the backing 110 of the kinesiology tape. For example, the comb 205 can be made of metal, such as steel or copper, wood, plastic or any other material that is sufficiently rigid.

FIG. 2 shows that, in at least one implementation, the comb 205 can include a spine 205a. In particular, the spine 205a holds in place a number of teeth 205b. The teeth 205b remove all or part of the adhesive previously applied to the backing 110 as the backing 110 passes through the adhesive applicator 200. The teeth 205b can be separated by any desired amount and the separation need not be constant. Additionally or alternatively, the teeth 205b need not all be the same size depending on the desired pattern.

In at least one implementation, the width of the comb 205 indicates the width of the area on the surface of the backing 110 which can receive adhesive. For example, the width of the comb 205 may be greater than the width of the backing 110 to which adhesive may be applied. I.e., if the width of the comb 205 is 950 millimeters, the width of the surface to which adhesive may be applied can be 900 millimeters.

Further, lateral movement of the teeth 205b can allow a periodic or non-periodic pattern to be created in the adhesive. For example, regular reciprocating motion of the teeth 205b can create a sine wave pattern in the adhesive. Additionally or alternatively, lateral motion of the teeth 205b can create a pattern, such as a step frequency pattern, as discussed below. Patterns in the adhesive may provide for better adhesion between the kinesiology tape and the user's skin. For example, patterns can allow some of the tracks in the adhesive to point horizontally and others to point vertically. Patterns can allow the kinesiology tape to resist forces caused by a user's movement in any direction.

FIG. 2 also shows that the adhesive applicator 200 includes a stand 210 and a shaft 215 attached to the comb 205. The stand 210 and the shaft 215 can support the comb 205 as the backing 110 passes along the comb 205. In at least one implementation, the shaft 215 is secured within the stand 210. Securing the shaft 215 within the stand 210 can allow the comb 205 to move laterally in relationship to the stand 210. Lateral movement of the comb 205 can allow for the production of patterns in the adhesive applied to the backing 110 without requiring movement of the backing 110, as discussed above. These patterns may provide better adhesion of the kinesiology tape to a user's body, as discussed above.

FIG. 2 further shows that the shaft 215 is connected to an erratic cam 220. In particular, the shaft 215 can be connected via a beam 225 and a connector 230, as shown in FIG. 2, or can be directly connected to the erratic cam 220. For example, connecting the shaft 215 to the erratic cam 220 via a beam 225 and a connector 230 can allow for vertical variations in the movement of the erratic cam without disrupting the lateral movements of the comb 205. For example, variations in the vertical alignment of the erratic cam 220 are translated to vertical movement in the beam 225. The vertical movement of the beam 225 passes through the connector 230 while producing little or no vertical movement of the connector 230 or the shaft 215. Thus, variations in the vertical alignment of the erratic cam 220 have no effect on lateral movement of the shaft 215 and, therefore, in the horizontal movement of the comb 205.

The rotation speed of the erratic cam 220 correlates to the number of reciprocations of the comb 205 and the frequency of the adhesive pattern on the backing 110. For example, when the erratic cam 220 rotates 60 times/minute, the comb completes 60 patterns per minute. If the backing 110 passes through the adhesive applicator 200 at 3.0 meters/minute, the pattern is repeated 20 times for each meter of the backing 110 (and, therefore, kinesiology tape). I.e., the adhesive pattern repeats every 5 centimeters.

FIG. 2 also shows that a rod 235 can rotate the erratic cam 220. The rod is rotated through a mechanical means. Rotation of the rod 235, and therefore the erratic cam 220, is translated to horizontal motion of the shaft 215, and therefore the comb 205, as discussed below. FIG. 2 shows that the shaft 235 need not be located in the center of the erratic cam 220, thus inducing lateral movement in the beam 225 and, thus, the comb 205, as discussed below.

In addition, the adhesive applicator 200 may include a drying area with one or more drying zones. The drying area can be used to evaporate some or all of the solvent from the adhesive. For example, the drying area can be 16 meters in length and can include eight drying zones with varying temperatures and temperature tolerances. The temperature in the drying zones can include: zone 1—100±5° C.; zone 2—110±5° C.; zone 3—130±5° C.; zone 4—130±5° C.; zone 5—130±5° C.; zone 6—130±5° C.; zone 7—125±5° C.; and zone 8—120±5° C.

In at least one implementation, after the adhesive is applied to the backing 110 and passes through the drying area, the backing 110 is applied to the kinesiology tape. Pressure and heat can ensure bonding between the kinesiology tape and the backing 110. Bonding the backing 110 to the kinesiology tape can protect the adhesive until a user removes the backing 110 for application of the kinesiology tape.

Accordingly, adhesive can be applied to the backing 110 and the backing 110 bonded to the kinesiology tape while the backing 110 and the kinesiology tape move through the adhesive applicator 200. Therefore, the production time of the kinesiology tape can be decreased and the efficiency of the production increased.

Figure 3:
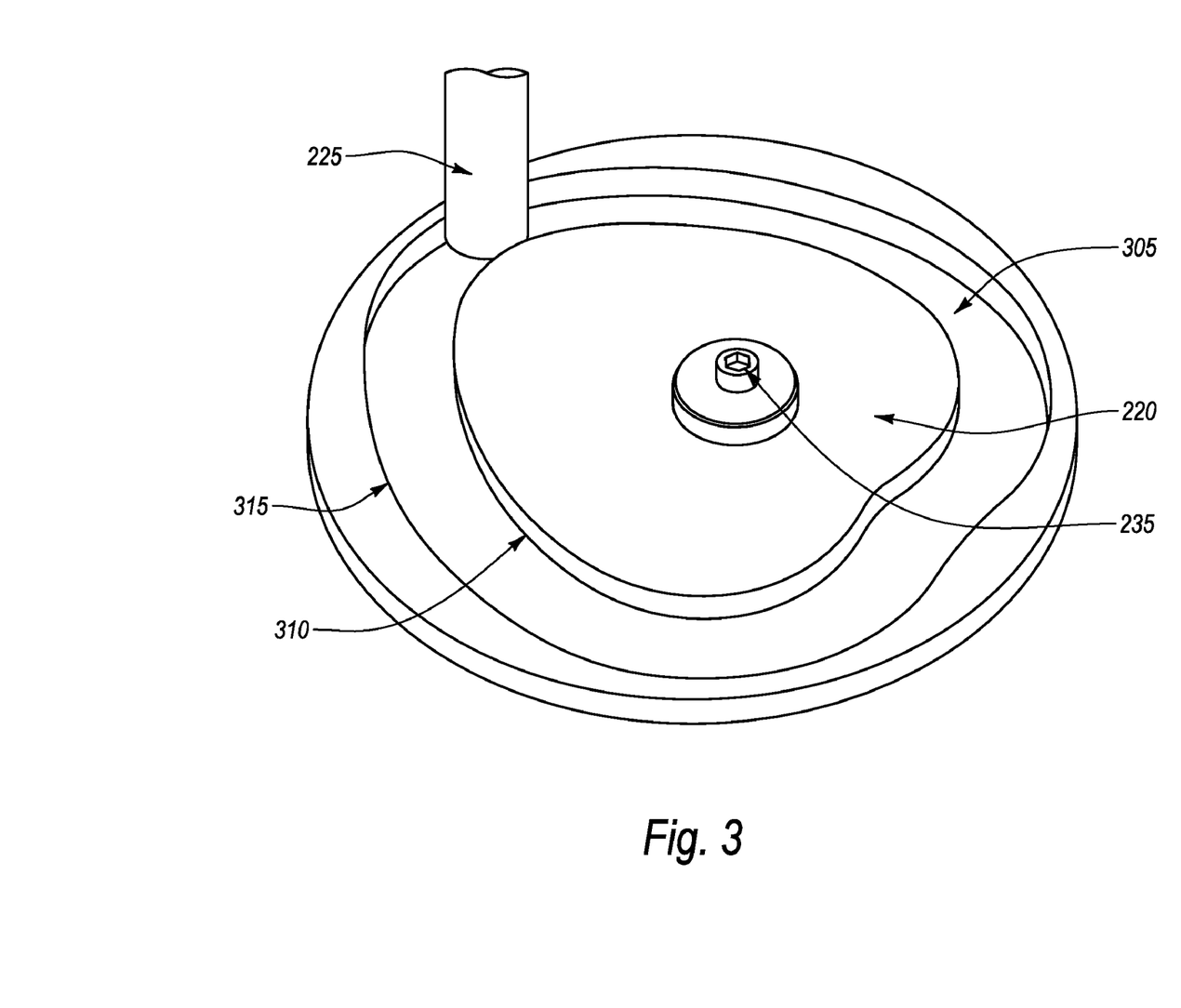
FIG. 3 illustrates an example of an erratic cam in accordance with an implementation of the present invention.

FIG. 3 illustrates an example of an erratic cam 220 in accordance with an implementation of the present invention. FIG. 3 shows that, in at least one implementation, the erratic cam 220 can translate circular movement induced in the erratic cam 220 to reciprocating movement of a beam 225. For example, the erratic cam 220 can include a projecting part of a rotating device that can strike the beam 225 at one or more points on its circular path. In particular, the erratic cam 220 can be an eccentric disc or other shape that produces a smooth reciprocating motion in the beam 225 which is in contact with the erratic cam 220. Additionally or alternatively, the erratic cam 220 can have a number of features which produce variations in the motion of the beam 225 from a straight reciprocating motion.

FIG. 3 shows that rotation of the erratic cam 220 can be induced by rotation of the rod 235, which is connected to the erratic cam 220. FIG. 3 further shows that, in at least one implementation, the rod 235 need not connect to the erratic cam 220 directly in the center of the erratic cam 220. Additionally or alternatively, the rod 235 can connect to the erratic cam 220 in the center, with the sides of the erratic cam 220 moving the beam 225 in a reciprocating manner.

FIG. 3 shows that, in at least one implementation, the erratic cam 220 includes a groove 305. The groove 305 can include an inner edge 310 and an outer edge 315. The groove 305 and its edges 310 and 315 retain a portion of the beam 225 such that rotation of the erratic cam 220 induces lateral movement in the beam 225. Additionally or alternatively, either the inner edge 310 or outer edge 315 of the groove 305 need not be present. For example, a mechanism, such as a spring or other device, can provide constant force toward the erratic cam 220, pushing the beam 225 against the inner edge 310 of the groove 305. Thus, the inside edge 310 can provide the guidance necessary to provide the desired lateral motion of the beam 225, without the presence of the outer edge 315. Alternatively, a mechanism, such as a spring or other device, can provide constant force away from the erratic cam 220, pushing the beam 225 against the outer edge 315 of the groove 305. Thus, the outside edge can provide the guidance necessary to provide the desired lateral motion of the beam 225, without the presence of the inner edge 310.

Figure 4:
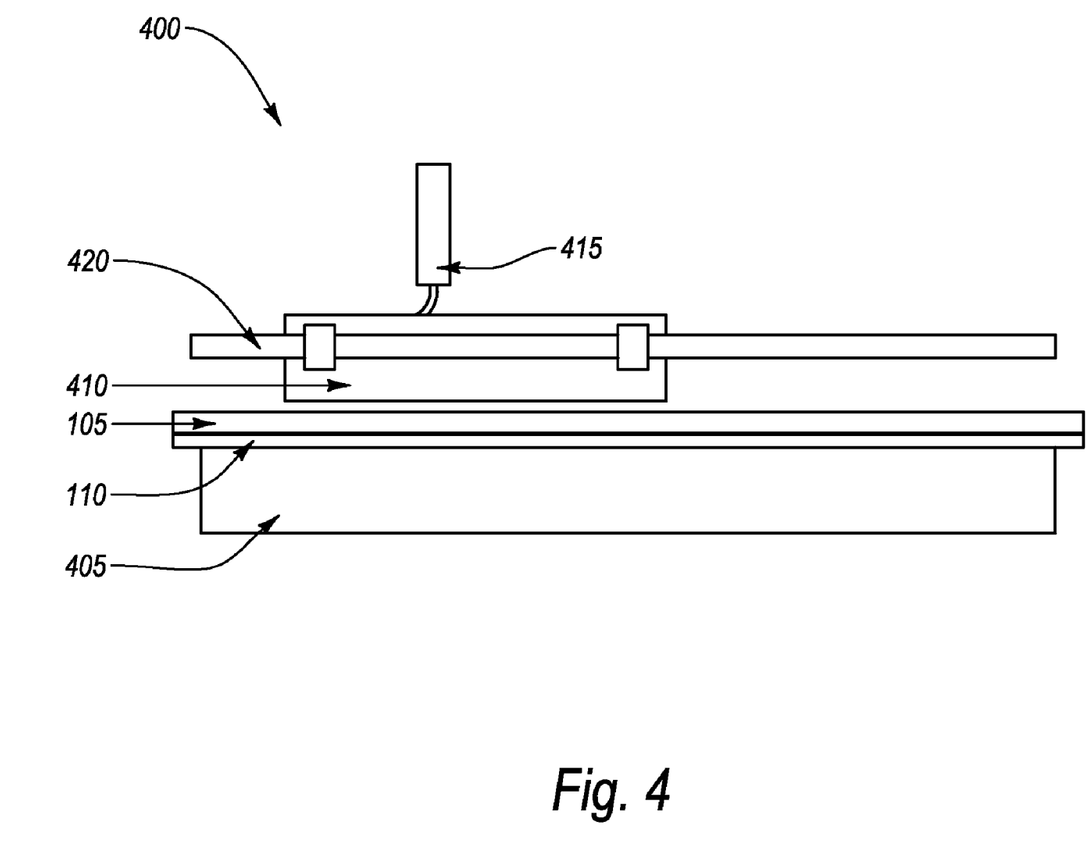
FIG. 4 shows an example of a printing device for printing on kinesiology tape in accordance with an embodiment of the present invention.

FIG. 4 shows an example of a printing device 400 for printing on kinesiology tape 105, without bleeding through to the backing 110, in accordance with an embodiment of the present invention. In at least one implementation, the printing device 400 can print on the kinesiology tape 105 using a screen, or silk-screen, printing method. Screen printing includes a printing technique that uses a woven mesh to support an ink-blocking stencil, as discussed below with reference to FIG. 5. The attached stencil forms open areas of mesh that transfer ink as a sharp-edged image onto a substrate.

FIG. 4 shows that, in at least one implementation, the printing device 400 includes a surface 405 over which one or more ribbons of kinesiology tape 105 pass. The surface 405 can guide the kinesiology tape 105 to the proper position and provide resistance against pressure applied during the printing process. The surface 405 can be used to move the kinesiology tape 105. For example, the surface 405 can include a conveyor or other surface capable of movement. Additionally or alternatively, the kinesiology tape 105 can be drawn through the printing device 400 by an external mechanism.

FIG. 4 shows that, in at least one implementation, the printing device 400 also includes a tray 410. In particular, the tray 410 acts as a reservoir for the ink used during the printing process. The ink includes any suitable material for dyeing or coloring the kinesiology tape 105. For example, the ink can include an aqueous ink. In at least one implementation, aqueous ink can include water, synthetic resin and pigment. Additionally or alternatively, the tray 410 also can include the screen to be used in the printing process, as discussed below.

In at least one implementation, the tray 410 is placed in a position over the kinesiology tape 105 without making contact with the kinesiology tape 105. Ink is then placed within the tray 410, on top of the screen. The operator then uses a squeegee 415, which can include a rubber blade, to move the mesh down to the kinesiology tape 105 and moves the squeegee 415 over the screen. Movement of the squeegee 415 pushes ink into the mesh openings and the ink is, in turn, pumped or squeezed by capillary action to the kinesiology tape 105 in a controlled and prescribed amount. The thickness of the mesh, the amount of pressure applied by the squeegee 415, the viscosity of the ink and other factors control the amount of ink in the mesh. As the squeegee 415 moves along the screen, the tension of the mesh pulls the mesh up and away from the kinesiology tape 105 (called snap-off) leaving the ink on the kinesiology tape 105.

In at least one implementation, the tray 410 moves along a track 420 during the printing process. If the speed of the movement of the tray 410 along the track 420 matches the speed of the movement of the kinesiology tape 105 over the surface 405, the printing can occur without stopping the kinesiology tape 105. For example, if the printing device 400 can print five strips simultaneously, and can print 22 passes per minute, the printing device 400 can print on 110 strips of kinesiology tape 105 per minute. Accordingly, the manufacture of the kinesiology tape 105 can progress quicker and can be more efficient.

Figure 5:
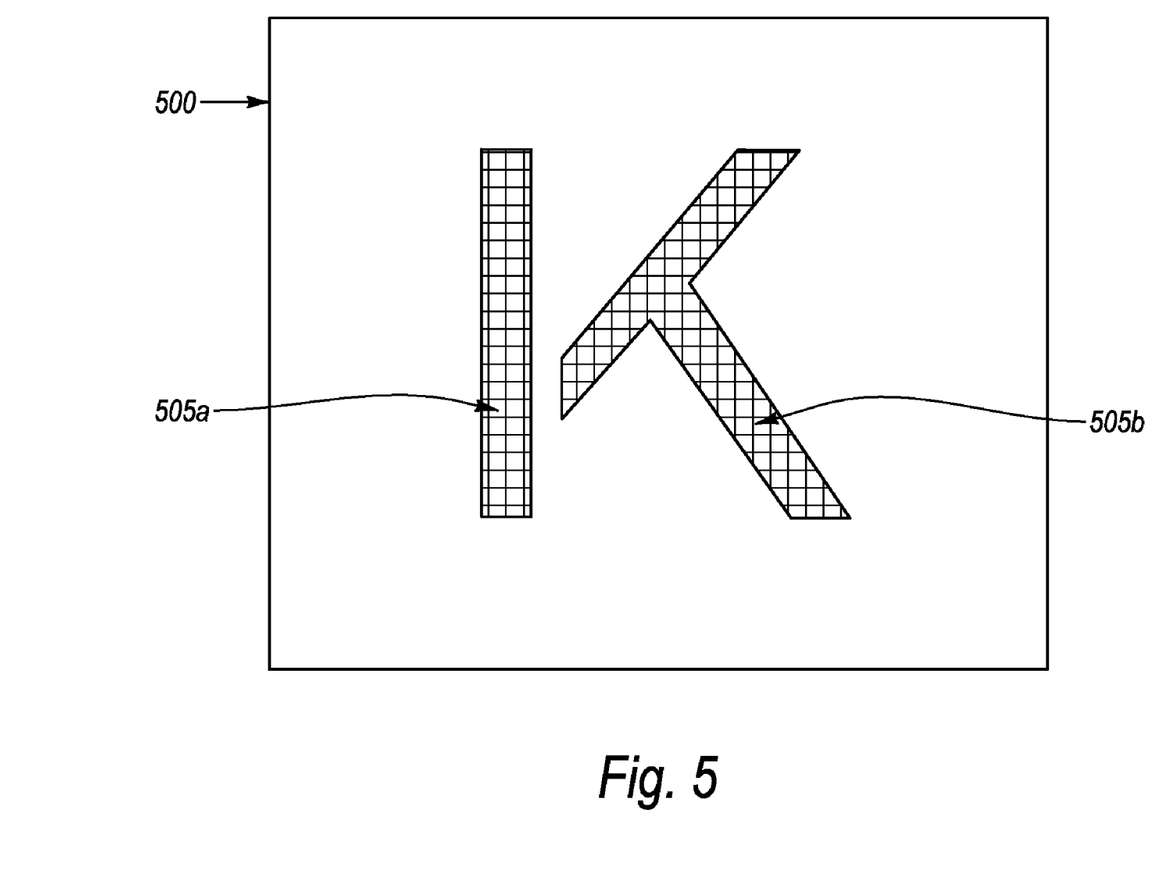
FIG. 5 illustrates an example of a print screen in accordance with an implementation of the present invention.

FIG. 5 illustrates an example of a print screen 500 in accordance with an implementation of the present invention. A non-permeable material blocks areas of the print screen 500 to form a stencil, which is a negative of the image to be printed; that is, the open spaces are where the ink will appear. A print screen 500 is made of a piece of porous, finely woven fabric called mesh stretched over a frame of aluminum or wood.

In at least one implementation, the mesh material can be made of any material which is porous enough to allow at least a portion of the ink to pass through the mesh and which is nonporous enough to retain the non-permeable material where it is desired. For example, the mesh can include steel, nylon, and polyester. Additionally, the width of the fibers can determine the amount of ink which passes through the screen. For example, the gap between the individual threads of the mesh can be 0.106 millimeters.

In at least one implementation, different colors can be printed using different screens 500. For example the first portion of open space 505a can be included in a first screen 500 and used to print a first color while the second portion of open space 505b can be included in a second screen 500 and used to print a second color. Additionally or alternatively, the screen 500 can include more than one open space 505 for multiple printings on different strips simultaneously.

Figure 6:
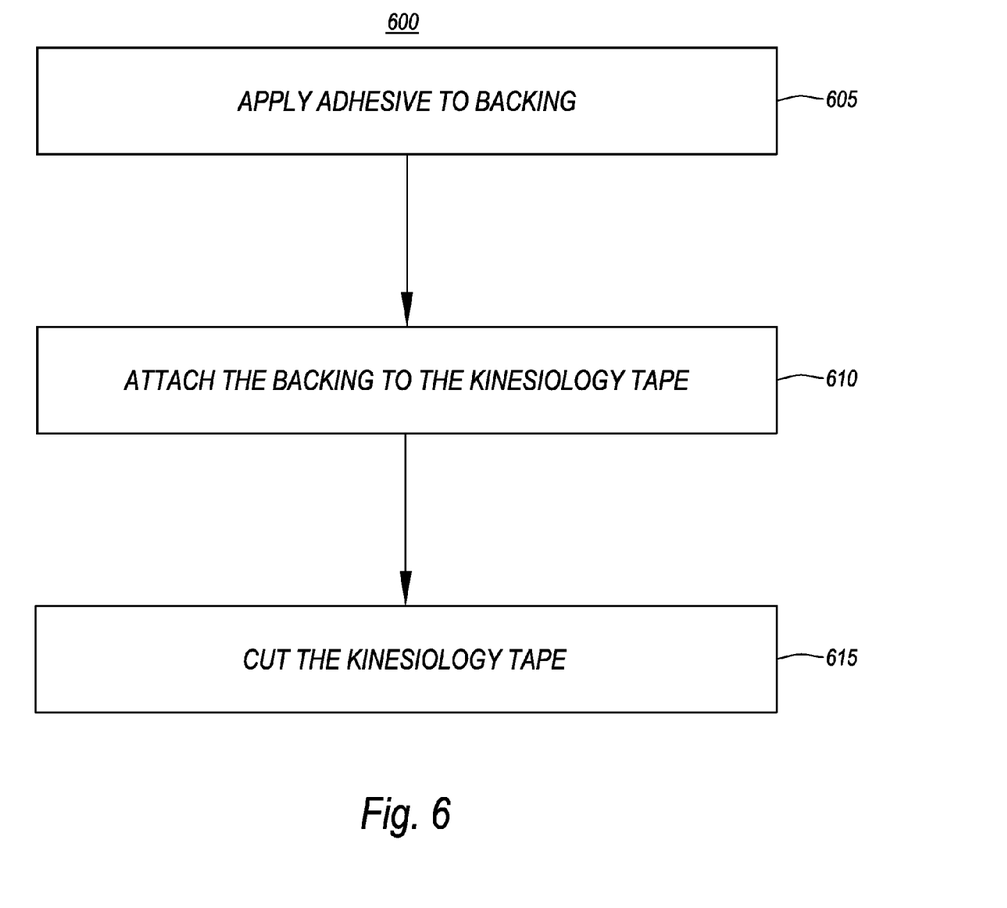
FIG. 6 is a flow chart illustrating a method for manufacturing kinesiology tape.

FIG. 6 is a flow chart illustrating a method 600 for manufacturing kinesiology tape. The method 600 can be implemented using the variable depth die cut 100 of FIGS. 1A and 1B, the adhesive applicator 200 of FIG. 2 and the printing device 400 of FIG. 4 or by other systems. Therefore, the method 600 will be described, exemplarily, with reference to the variable depth die cut 100 of FIGS. 1A and 1B, the adhesive applicator 200 of FIG. 2 and the printing device 400 of FIG. 4. Nevertheless, one of skill in the art can appreciate that the method 600 can be accomplished using other apparatus than those described with reference to FIGS. 1, 2 and 4.

The method 600 includes applying 605 adhesive to backing material. For example, in at least one implementation, the adhesive applicator 200 of FIG. 2 can be used to apply adhesive to backing 110 to be applied to a strip of kinesiology tape. Adhesive on a strip of kinesiology tape can allow a user to easily apply the tape as need requires, without additional materials. The backing 110 can protect the adhesive and prevent drying of the solvent until a user is ready to apply the kinesiology tape.

The method 600 also includes attaching 610 the backing to kinesiology tape. For example, the adhesive can include pressure-sensitive adhesive. Pressure sensitive adhesive is adhesive which forms a bond when pressure is applied. I.e., no solvent, water, activator chemicals, heat or other activating agent is needed to activate the adhesive. In at least one implementation, the degree of bonding is influenced by the amount of pressure which is used to apply the adhesive to the surface of the backing 110. In at least one implementation, attaching 610 the backing to kinesiology tape can include applying pressure to the kinesiology tape and backing to activate the pressure sensitive adhesive.

The method 600 further includes cutting 615 the kinesiology tape. In at least one implementation, cutting 615 the kinesiology tape can include using a die cut, such as the die cut 100 of FIG. 1. For example, FIGS. 1A and 1B show that in at least one implementation, the die 100 can cut, shape and form a strip of kinesiology tape 105, and the backing 110 attached to the kinesiology tape 105, during the manufacture thereof. In particular, the die 100 can cut a single large ribbon of kinesiology tape 105 into a number of smaller strips. Additionally or alternatively, the die can cut or perforate the backing 110 of the kinesiology tape 105, allowing a user to separate individual strips of kinesiology tape 105 from one another as needed.

The method 600 can also include printing a logo on the kinesiology tape. The printing can be accomplished using a printing device, such as the printing device 400 of FIG. 4. In at least one implementation, the printing device 400 can print on the kinesiology tape 105 using a screen, or silk-screen, printing method. Screen printing includes a printing technique that uses a woven mesh to support an ink-blocking stencil, as discussed below with reference to FIG. 5. The attached stencil forms open areas of mesh that transfer ink as a sharp-edged image onto a substrate.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of manufacturing kinesiology tape, wherein the method comprises:
   applying adhesive to backing to be placed on kinesiology tape using an adhesive applying device, the adhesive applying device including:
      an applicator, wherein the applicator is configured to apply glue to one surface of the backing;
      a comb, wherein the comb is configured to produce a pattern in the adhesive as the backing moves past the comb, wherein the comb includes:
         a spine; and multiple teeth protruding from the spine, wherein the teeth remove adhesive from the backing;

a shaft, wherein the shaft is attached to the spine of the comb;

an erratic cam, wherein the erratic cam is configured to move the shaft on the comb to produce motion in the comb; and a motor for rotating the erratic cam attaching the backing to kinesiology tape;

cutting the kinesiology tape using a continuous feed variable depth die cut for use in cutting kinesiology tape, the die cut including:

a housing, wherein the housing includes:
   a first opening, wherein the first opening is configured to allow the kinesiology tape to enter the housing; and
   a second opening, wherein the second opening is configured to allow the kinesiology tape to exit the housing;

a roller inside the housing, wherein the roller is configured to rotate as the kinesiology tape passes over the roller;

a die formed on the outer surface of the roller, wherein the die includes a cutting edge for cutting the kinesiology tape and wherein the cutting edge is formed in the shape of the strip of kinesiology tape to be cut; and a surface inside the housing, wherein the kinesiology tape passes over the surface when the kinesiology tape is being cut; and printing a logo on the kinesiology tape using a printing device for printing on kinesiology tape, the printing device including:

a printing surface, wherein the kinesiology tape moves across the printing surface as the printing occurs;

a tray, wherein the tray is configured to hold the ink;

a woven mesh, wherein the woven mesh forms at least a portion of the bottom of the tray and wherein the woven mesh includes:
   an ink-blocking stencil, wherein the stencil includes blocked mesh that prevents the extrusion of ink; and
   an open area of mesh, wherein the open area of the mesh allows the extrusion of ink onto the kinesiology tape; and a squeegee, wherein the squeegee moves across the mesh forcing ink through the open area of the mesh and forces the mesh onto the kinesiology tape.

2. The method of claim 1, wherein the woven mesh is made of nylon.

3. The method of claim 2, wherein the woven mesh includes at least one gap, wherein the gap is 0.106 mm.

4. The method of claim 1, further comprising a motor for moving the tray as the squeegee moves across the mesh.

5. The method of claim 4, wherein the tray moves at the same rate at which the kinesiology tape passes over the surface, such that the relative position of the tray to the kinesiology tape is fixed during at least a portion of the printing process.

6. The method of claim 1, further comprising a drying device, wherein the drying device includes:

an ultraviolet light, wherein the ultraviolet light is configured to speed the drying of the ink: and a vacuum, wherein the vacuum removes the air surrounding the printed ink to speed the drying of the ink.

* * * * *